United States Patent [19]
Clyde et al.

[11] Patent Number: 4,530,763
[45] Date of Patent: Jul. 23, 1985

[54] METHOD FOR TREATING WASTE FLUID WITH BACTERIA

[76] Inventors: Robert A. Clyde, P.O. Box 983, Asheville, N.C. 28802; Andrew Whipple, P.O. Box 276, Montreat, N.C. 28757

[21] Appl. No.: 512,534

[22] Filed: Jul. 11, 1983

[51] Int. Cl.³ .................. C02F 3/04; C12N 11/08; D06M 16/00; C12R 1/38
[52] U.S. Cl. .................. 210/610; 210/611; 210/615; 210/619; 210/912; 210/913; 423/DIG. 17; 423/3; 423/23; 423/53; 423/62; 435/180; 435/264; 435/874
[58] Field of Search ............ 210/601, 610, 611, 615, 210/619, 150, 151, 912, 913, 505, 508; 423/DIG. 17, 3, 53, 23, 62, 6; 435/174, 180, 264, 822, 874–877; 75/101 R, 84.1 A; 252/631, 632

[56] References Cited

U.S. PATENT DOCUMENTS

| 4,165,281 | 8/1979 | Kuriyama et al. | 210/150 |
| 4,269,719 | 5/1981 | Yamamoto | 210/150 |
| 4,292,408 | 9/1981 | Zimmermann et al. | 423/DIG. 17 |
| 4,320,093 | 3/1982 | Volesky et al. | 423/6 |
| 4,416,993 | 11/1983 | McKeown | 210/611 |

FOREIGN PATENT DOCUMENTS 53-59254  5/1978  Japan ...................... 210/610

OTHER PUBLICATIONS

Hollo J. et al.; "Denitrification and Removal of Heavy Metals from Waste Water by Immobilized Microorganisms" found in Immobilized Microbial Cells, American Chemical Society, 1979 (pp. 73-86).
Tuovinen O. H. et al., "Use of MicroOrganisms for the Recovery of Metals"; Int. Metallurgical Reviews, 1974 Review 179 (pp. 21-31).

Primary Examiner—Benoit Castel
Attorney, Agent, or Firm—D. I. Hague

[57] ABSTRACT

A method for treating waste fluids to remove selected chemicals such as minerals and metals wherein a bacterial culture that will attach to a selected chemical is transferred to a nutrient medium for a time period sufficient to produce satisfactory bacterial cell growth. The bacterial cells are then attached to a porous fiber webbing supported in a suitable container and the nutrient medium is then withdrawn from the container and waste fluid introduced into the container for a period of time sufficient to attach the chemical to the bacterial cells. The waste fluid is then removed from the container and the chemical separated from the fiber webbing.

14 Claims, 2 Drawing Figures

METHOD FOR TREATING WASTE FLUID WITH BACTERIA

FIELD OF THE INVENTION

The present invention relates to methods for treating waste fluids. More particularly, the invention relates to improved methods for treating waste fluids with bacteria to remove selected chemicals such as minerals and metals.

DESCRIPTION RELATIVE TO THE PRIOR ART

Many industrial processes require large amounts of water which become contaminated with dissolved minerals and metals. The impure water from these processes requires treatment to meet the increasingly strict requirements of various government environmental protection agencies. Storage of the waste water in holding ponds for material settling and degradation of the contaminants is an economic liability since it frequently requires several years (in some cases a decade or more) to accomplish as well as an environmental hazard due to leaching of the contaminants. Furthermore, efficiency and cost considerations have demanded alternative routes which would enable the recovery of valuable metals or their compounds in the waste water.

Drobot in U.S. Pat. Nos. 4,293,333 and 4,293,334 discloses a process for separating metals from industrial waste water with a selected fungi, or a selected killed fungi, respectively, to effect extraction of the metals. The recovered metal is deposited in the biomass and may be recovered therefrom by relatively simple methods. The principal disadvantages of the Drobot process are that because fungi have complex life cycles and may involve several different forms (filaments, spores, and yeasts), (1) fungi are difficult to prepare and (2) take a long time to grow. Drobot, for example, discloses that useful fungi were cultured in a soymeal medium on a rotary shaking machine at 28° C. for *six* days and then centrifuged at 6,000 rpm. A 6,000 rpm centrifuge is available in a laboratory but would be very expensive on a commercial scale.

U.S. Pat. No. 3,937,520 discloses a process for leaching minerals from subterranean formations using a relatively low initial volume of sulfuric acid and low volumes of sweep or displacement fluids. This is accomplished by using a biological agent such as bacteria to produce in situ, the sulfuric acid leaching agent in sufficient strength to solubilize the desired mineral.

SUMMARY OF THE INVENTION

The present invention provides a simple, inexpensive, yet highly efficient process for removing selected chemicals, such as metals and minerals, from industrial waste fluids. This is accomplished in accordance with the present invention by incubating a selected bacterial culture which will attach the chemical desired to be removed from the waste fluid. A nutrient medium for the bacteria is sterilized, innoculated with the bacteria, and incubated for a sufficient period of time to produce satisfactory bacterial growth. The bacterial cells are attached to a porous substrate, comprising a multiplicity of high area, sterilized fibers supported within the container, preferably during the bacterial growth period, by moving one of the bacteria and the porous substrate relative to each other. The nutrient medium is then removed from the container and the waste fluid introduced and contacted with the bacteria for a period of time sufficient to attach the selected chemical to the bacterial cells. The attached chemical is then recovered by simple methods, for example, by burning the fiber substrate, by physically detaching the bacteria (which contain the chemical) from the fibers, or by chemically removing the chemical from the attached bacterial cells with a solution of sodium carbonate.

The invention and its features and advantages will become more apparent by referring to the accompanying drawings and to the ensuing detailed description of the preferred embodiments.

DETAILED DESCRIPTION OF THE PREFERRED EMBODIMENTS

In the process of the present invention it is first necessary to prepare a culture by sterilizing a nutrient medium, innoculating it with suitable bacteria, and incubating at a suitable temperature until sufficient bacterial growth has occurred. This nutrient medium, depending upon the type of bacteria to be grown, may, for example, consist of sugar, yeast extract, $KH_2PO_4$, $(NH_4)_2SO_4$ and $MgSO_4$, or could simply be nutrient broth, as clearly described and understood by those skilled in the biological art. A selected bacterial culture which will attach to the chemical desired to be removed from the waste water is then transferred, in any suitable manner, into the nutrient solution and incubated at a suitable temperature in a container having sterilized porous fiber webbing supported therein. Useful bacteria include *Zymomonas mobilis* strain 10988 which attaches to clay attapulgite (a mineral consisting of magnesium and aluminum silicate), *Pseudomonas aeruginosa* which attaches to uranium and chromium, *Pseudomonas fluorescens* which attaches to silver and uranium and *Thiobacillus ferrooxidans* which attaches to palladium. In the case of *Z. mobilis* a suitable temperature is between 30 and 35 degrees centigrade (°C.). In the case of *P. aeruginosa* a suitable temperature is approximately 37° C., in the case of *P. fluorescens* a suitable temperature is approximately 30° C., and in the case of *T. ferrooxidans* a suitable temperature is approximately 22° C.

The porous fiber webbing may be of any suitable material. Useful fiber webbing materials include cotton, polyester, Orlon ® acrylic fiber and Dacron ® yarn, nylon, rayon, acetate, wool, polypropylene or any combination of such materials. In certain applications, such as those involving acid waste waters or nutrient mediums, organic fiber webbing will not be satisfactory since the acid will operate on such fibers. In such applications fiber webbing of Dacron ® or Orlon ® is preferred. The fiber webbing is preferably about ¼ inch or less apart and made of fiber aggregates such as strings or yarns about ⅛ inch in diameter or less, each composed of many much smaller diameter fibers.

Figure 1:
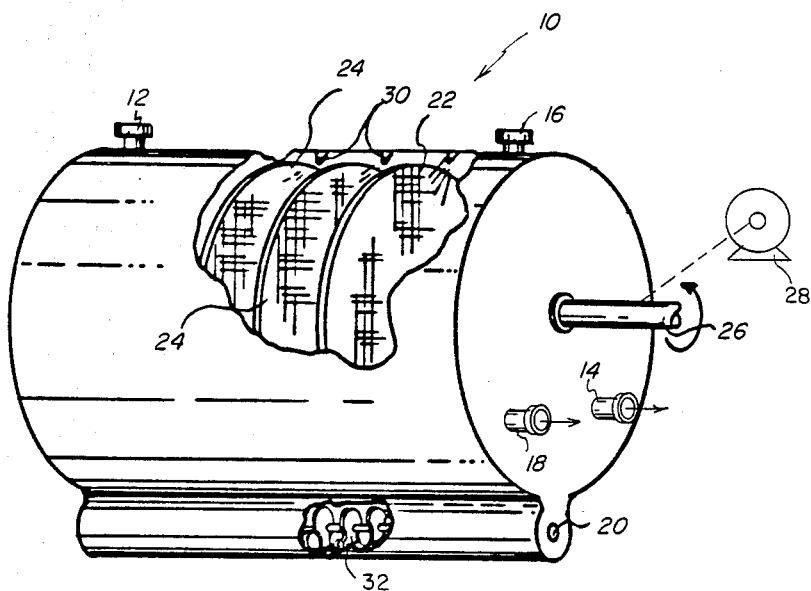
FIG. 1 is a perspective view of one embodiment of apparatus suitable for carrying out the process of the present invention.
Figure 2:
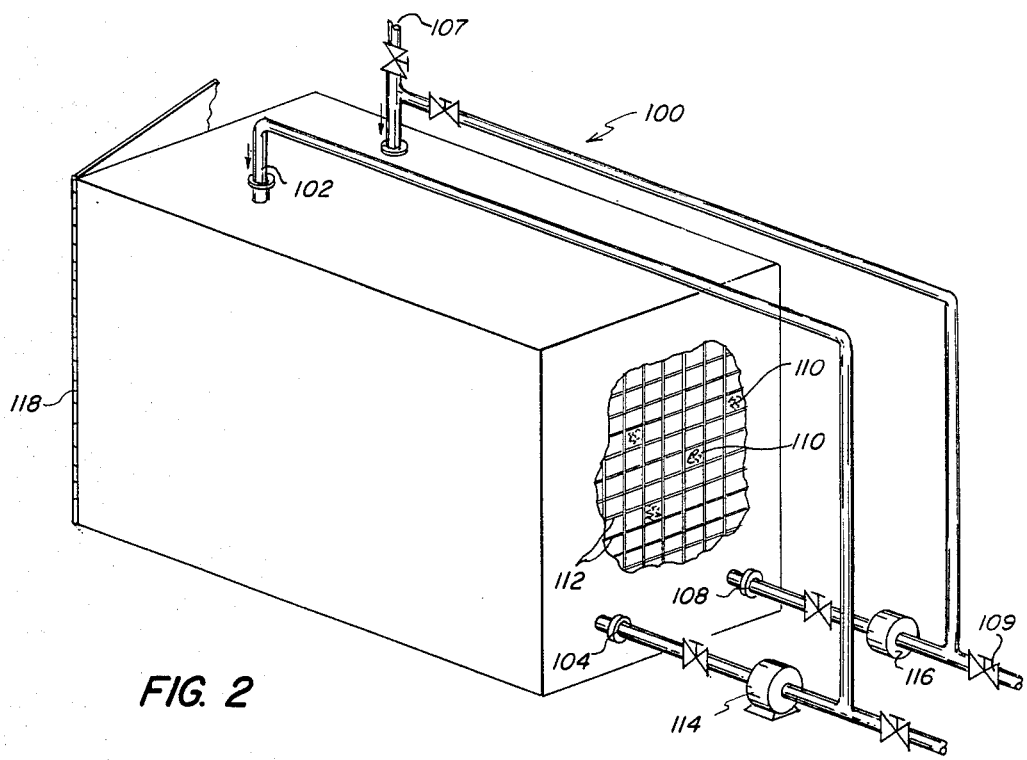
FIG. 2 is a perspective view of another embodiment of apparatus suitable for carrying out the process of the present invention.

The incubated culture in the container starts a rapid, exponential growth attached to the fiber webbing. To speed the reaction time and to aid bacterial attachment, the fiber webbing is moved relative to the nutrient solution as described hereinbelow with reference to FIG. 1 or, as described with reference to FIG. 2, the nutrient solution is moved relative to the fiber webbing. The rate of relative movement between the nutrient solution and the fiber webbing should be sufficient for thorough mixing without causing the bacterial cells to become detached from the webbing. Tests have shown that bacteria detachment occurs at a certain definite rate of movement. A test suitable for use in the present invention to evaluate the adhesion between a selected bacteria and a selected fiber webbing consists of pumping the bacterial cells up through an orifice and then radially across a plate to which the fiber webbing is attached. At a particular pumping rate the shear forces are too great and the bacteria become detached from the webbing. The optimal rate of relative motion between the nutrient solution and the webbing must then be slightly less than the above noted rate. A device for measuring bacteria adhesion is commercially available from Dr. Fowler of the Chemical Engineering Department at the University College of Swansea in England or from an associated company.

After sufficient growth of bacterial cells, the nutrient solution is removed from the container and the waste fluid is introduced with relative motion by the same mechanism which provided relative motion between the nutrient solution and the fiber webbing (i.e., by moving the fiber webbing relative to waste fluid as illustrated in FIG. 1 or by moving the waste fluid relative to the fiber webbing as illustrated in FIG. 2.) It is believed that the chemical attaches to the bacterial cells or the fiber webbing by electrical attraction (the bacteria are slightly negative and the chemical is positively charged) and/or by entrapment.

After a period of time sufficient to attach the desired chemical in the waste fluid to the bacterial cells, the waste fluid is removed from the container and the chemical recovered by simple procedures known in the art, for example, by burning the fiber webbing or by washing the fibers to physically detach the bacteria and/or chemical.

With reference now to the drawings, FIG. 1 shows a container 10 having a nutrient input port 12 and an output port 14, a waste fluid input port 16 and an output port 18 and a chemical output port 20. A porous, sterilized fiber webbing 22 is mounted on a plurality of supported filters 24 which are rotably mounted on a shaft 26. In operation, the fibers are sterilized and the container 10 is ¾ filled with nutrient solution and a selected bacteria is added. The filters 24 and the fiber webbing 22 supported thereon are then rotated by a motor 28 to promote bacterial cell growth and to attach the bacterial cells to the fiber webbing. When there is sufficient growth of bacterial cells to attach the desired chemical, the nutrient solution is pumped out of the container 10 through the output port 14 by means (not shown) and the waste fluid containing the desired chemical is introduced into the container through the input port 16. Filters 24 and the fiber webbing 22 are again rotated. The unit can be run continuously by pumping waste fluid in through port 12 and out through port 18 by means (not shown). The waste fluid is then pumped out of the container 10 through the output port 18 by means (not shown). Nozzles 30 are then turned on to wash off the filters 24. A screw conveyor 32 is also turned on to remove through the output port 20 the biomass (bacterial cells and chemical) that is washed down to the bottom of the container 10.

Instead of moving the fiber webbing, the nutrient solution can be moved relative to the webbing as shown in FIG. 2. A container 100 includes a nutrient input port 102 and an output port 104 and a waste fluid input port 107 and an output port 108. Sterilized fiber webbing 110 is mounted on a plurality of supported wires 112. In operation the fibers are sterilized. A sterile nutrient solution and a selected bacteria are then added to the container through input port 102. A motor 114 is turned on to slowly circulate the nutrient solution through the container, out the output port 104 and back into the input port 102. This circulatory motion promotes rapid growth of bacterial cells and attaches the cells to the fiber webbing. The nutrient solution is then pumped out of the container through the output port 104. Waste fluid is then pumped into the container through input port 107, circulated through the container 100, pumped out of the container through the output port 108 and pumped back into the container through the port 107 by a motor 116. The unit can be run continuously by pumping in waste fluid through port 107 by means not shown and out through port 109 by pump 116. After the selected chemical in the waste fluid has attached to the bacterial cells, the waste fluid is pumped out of the container through the output port 108. A hinged rear door 118 of the container 100 is opened, and the fiber webbing removed and replaced for treatment of additional waste fluid. The chemical is recovered from the bacterial cells on the removed fiber webbing either by scraping the fibers, by burning the fibers, or leaching with $Na_2CO_3$.

The following examples will serve to further illustrate the present invention.

Example No. 1

A culture of *Zymomonas mobilis* strain 10988 obtained from the American Type Culture Collection was transferred from a slant to about 5 ml of 2% sugar and ½% yeast extract, incubated overnight at 30° C. until $CO_2$ bubbles occurred, then put into an Erlenmeyer flask with 5% sugar at 30° C., stirred with a magnetic stirrer for 6 hours, until bubbles occurred, then put into 400 ml of 10% sugar and stirred 4 hours. This 400 ml was then placed in a rotating biological contactor consisting of parallel discs of polyester, and stirred for several hours at 26 rpm until the bacteria attached to the fibers. The sugar solution was washed out of the reactor by flushing with water several times, leaving the bacteria on the fiber. A waste water sample comprising attapulgite from 0.2 to 2 microns in size was put in the reactor and stirred for only 3 minutes and poured into a 100 ml graduate. In 3½ hours there was 35 ml of clear solution on top. In 8 hours, 45 ml of clear solution, and in 10 hours, 58 ml of clear solution. When the untreated clay suspension was put directly into a 100 ml graduate, after 12 hours setting there was only 2 ml of clear solution on top and after 21½ hours only 6 ml of clear solution.

Example No. 2

A one-day old nutrient broth culture of *Pseudomonas aeruginosa* obtained from the American Type Cultural Collection was diluted with an equal volume of fresh nutrient broth culture. Sterilized Orlon® acrylic and Dacron® polyester fibers were suspended in the culture and anchored with stainless steel washers. As a control, sterilized Orlon® and Dacron® fibers were suspended in a second nutrient broth without bacteria.

The broth cultures were incubated at 37° C. for two days with gentle stirring by a magnetic stirring bar. The fibers were then removed from the broth cultures, gently rinsed with water, placed in a uranium acetate solution containing 30 parts per million uranium acetate for 2 hours, and then rinsed gently with water. The fibers that had been in the bacterial culture had more yellow color (indicating uranium) than the fibers that had been in the nutrient broth without bacteria.

Example No. 3

Two broth cultures of *Pseudomonas aeruginosa* were prepared. The next day the cultures were poured into a beaker containing about 300 ml of nutrient broth. The beaker was placed in a 37° C. incubator and stirred slowly by a magnetic stir bar. Sterilized fibers of Dacron ® and Orlon ® were suspended in the broth, held down with stainless steel washers. As a control a beaker containing nutrient broth without bacteria was placed in the incubator at the same time with suspended, sterilized fibers of Orlon ® and Dacron ®, with no stirring of the broth. The next day the fibers from both beakers were removed, dipped in water to rinse, placed in a 1% solution of $CrK(SO_4)_2.12H_2O$ for ½ hour and then rinsed gently. The fibers that had been in the bacteria culture were dark blue, indicating the presence of chromium. The fibers that had been in the nutrient broth without bacteria were white, indicating lack of chromium binding.

Example No. 4

0.055 gm of foil (75% palladium and 25% silver) dissolved in 5 ml of water and 3 ml of nitric acid and then diluted one to one. A medium (referred to as 9k) for *Thiobacillus ferrooxidans* was prepared as follows:

The following were dissolved in a total volume of 700 ml of distilled water and sterilized (solution A): 3.0 g $(NH_4)_2SO_4$; 0.1 g KCl; 0.5 g $K_2HPO_4$; 0.5 g $MgSO_4.7H_2O$; 0.01 g $Ca(NO_3)_2$; and 1.0 ml 10N $H_2SO_4$.

Solution B was prepared by making 300 ml of a 14.74% (w/v) solution of $FeSO_4.7H_2O$ and sterilizing it.

Complete medium 9k was prepared by mixing 7 parts of solution A with 3 parts of solution B using sterile technique to assure sterile medium 9k.

The bacteria were placed in the 9k medium and incubated at 22° C. Sterilized Orlon ® fibers were suspended in the 9k medium and coated with the bacteria by gently stirring the medium. The fibers were then rinsed, immersed in the palladium solution for 2½ hours with stirring, then removed and rinsed. The Orlon ® fibers had a dark brown color indicating palladium. A control run the same way with Orlon ® fibers immersed in a 9k medium without bacteria had no palladium, as indicated by the white color of the fibers.

Example No. 5

A one day old nutrient broth culture of *Pseudomonas fluorescens* obtained from the American Type Culture Collection was diluted with an equal volume of fresh nutrient broth culture. Sterilized Orlon ® and Dacron ® fibers were suspended in the culture. As a control, sterilized Orlon ® and Dacron ® fibers were suspended in a second nutrient bath without bacteria. The broth cultures were incubated at 30° C. for 2 days. The fibers were then removed from the broth cultures, gently rinsed with water, placed in a 1% silver nitrate solution overnight with gentle stirring and then rinsed gently with water. The fibers that had been in the bacterial culture had a dark brown color indicating silver. The fibers that had been in the nutrient broth without bacteria were white.

The process of the present invention provides a number of advantages over the processes of the prior art. Bacteria have a much simpler life cycle than fungi so they are easier to grow and it is easier to produce new strains. The use of fiber webbing provides a high contact area for the bacteria and for the chemical to be attached to the bacteria. Moving the bacteria and the nutrient solution relative to one another promotes a rapid growth of bacterial cells. By attaching to fibers, filtration of small particles is eliminated. It is believed that the relative motion reduces the fluid film around the bacterial cells so that the nutrients can reach the bacteria readily.

Example 6

Separate one day old cultures of *Pseudomonas putida* and *Pseudomonas cepacia* in 10 ml of nutrient broth were poured into 300 ml batches of sterile nutrient medium. Sterilized Orlon ® and Dacron ® fibers were suspended in the cultures, anchored at the bottom by stainless steel washers. As a control, sterilized Orlon ® and Dacron ® fibers were suspended in additional beakers of the same nutrient solutions, anchored in place by stainless steel washers. The cultures were then incubated for 2 days at +° C. to allow bacterial growth and attachment of the bacteria to the fibers. Gentle stirring by a magnetic stir bar was continuous during this incubation period and enhanced the even distribution of the bacteria onto the fibers.

At the end of this two day incubation the fibers, both those with the bacteria attached and the controls without any bacteria, were removed from the nutrient solutions, washed gently in water to remove the nutrient solution, and suspended in solutions of uranium, silver, and chromium for 24 hours, except for uranium which was for 2 hours, with stirring. The fibers were then washed gently in water and air dried. The fibers that had been in the bacterial cultures and had bacteria attached to them displayed a dark color characteristic of the metal solution, indicating the attachment of the metal to the bacteria on the fibers. The control fibers, without any bacteria, were the same color as before suspension in the metal solution, showing that the uptake of the metal by the fibers was due to the attached bacteria and not to properties inherent to the fibers themselves.

Example No. 7

A nutrient broth culture of *Pseudomonas aeruginosa* was prepared and sterilized Orlon ® and Dacron ® fibers were suspended in the culture and it was incubated at 37° C. for two days. As a control, fibers were also suspended in a nutrient bath without bacteria. The fibers were then removed from the cultures, gently rinsed, and placed in a solution of 100 parts per million of vanadium pentoxide overnight. They were then removed, rinsed gently with water and allowed to dry. The fibers that had been in the bacterial culture were yellow in color, indicating the presence of vanadium. Control fibers showed no color.

Example No. 8

A nutrient broth culture of *Pseudomonas putida* was prepared and sterilized Orlon ® and Dacron ® fibers were suspended in the culture and it was incubated at 30° C. for two days. As a control, fibers were also suspended in a nutrient bath without bacteria. The fibers were then removed from the cultures, gently rinsed, and placed in a solution of 100 parts per million of vanadium pentoxide overnight. They were then removed, rinsed gently with water and allowed to dry. The fibers that had been in the bacterial culture were yellow in color, indicating the presence of vanadium. Control fibers showed no color.

The invention has been described in detail with particular reference to illustrative preferred embodiments thereof, but it will be understood that variations and modifications can be effected within the spirit and scope of the invention.

I claim:

1. A process for removing a selected chemical from waste fluid comprising the steps of:
   (a) incubating a selected bacteria which will attach the selected chemical;
   (b) sterilizing, innoculating and incubating a nutrient medium for the bacteria;
   (c) placing the nutrient medium and the selected bacteria in a container having a plurality of porous support members supported therein, each of said support members having a webbing attached thereto comprising a multiplicity of high surface area fibers having a diameter of about ⅛ inch or less;
   (d) moving the support members and the nutrient medium relative to each other for a time period sufficient to produce satisfactory bacterial cell growth and to attach the bacterial cells to the webbing;
   (e) removing the nutrient medium from the container;
   (f) introducing the waste fluid into the container and removing the waste fluid and the support members relative to each other for a time period sufficient to attach the chemical to the bacterial cells; and
   (g) separating the selected chemical from the webbing.

2. The process according to claim 1 wherein the selected bacteria are of the genus Zymomonas and the selected chemical is clay attapulgite.

3. The process according to claim 1 wherein the selected bacteria are of the genus Thiobacillus, the fiber is Orlon ® and the chemical is palladium.

4. The process according to claim 1 wherein the selected bacteria are of the genus Pseudomonas and the fiber is selected from the group consisting of Dacron ® polyester and Orlon ® acrylic fiber and the chemical is chromium.

5. The process according to claim 1 wherein the selected bacteria are of the genus Pseudomonas, the fiber is selected from the group consisting of polyester, Orlon ® acrylic fiber and the chemical is uranium.

6. The process according to claim 1 wherein the selected bacteria is of the genus Pseudomonas and the chemical is silver.

7. The process according to claim 1 wherein said bacterial cell attaching step comprises moving the support members and the bacterial cells relative to each other at a speed slightly below the speed which the bacterial cells became detached from the support members and maintaining contact between the support members and the bacterial cells for a period of time sufficient to produce satisfactory bacterial cell growth.

8. The process according to claim 1 wherein said separating step comprises physically detaching the chemical from the fiber webbing.

9. The process according to claim 1 wherein said separating step comprises removing the fibers from the container and burning the fibers.

10. The process according to claim 1 wherein said separating step comprises removing said chemical from said fibers by washing.

11. The process according to claim 1 wherein said separating step comprises removing said chemical from said fiber with sodium carbonate.

12. The process according to claim 1 wherein the selected bacteria are of the genus Pseudomonas and the chemical is vanadium.

13. The process according to claim 1 wherein said bacterial cell and chemical attaching steps comprise rotating the support members within the container.

14. The process according to claim 1 wherein said chemical attaching step comprises continuously recirculating the waste fluid through the porous support members.

* * * * *